US008268628B1

(12) United States Patent
Pastrana-Rios et al.

(10) Patent No.: US 8,268,628 B1
(45) Date of Patent: Sep. 18, 2012

(54) METHOD FOR DETERMINATION OF PROTEIN, PEPTIDE OR PEPTOID AGGREGATION, STABILITY, AND VIABILITY AND SYSTEM USING THE SAME

(75) Inventors: Belinda Pastrana-Rios, Mayaguez, PR (US); Ibon LLoro-Manzano, Mayaguez, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 12/102,862

(22) Filed: Apr. 14, 2008

Related U.S. Application Data

(60) Provisional application No. 60/911,698, filed on Apr. 13, 2007.

(51) Int. Cl.
*G01N 33/00* (2006.01)
(52) U.S. Cl. .......................... 436/86; 436/164; 436/171
(58) Field of Classification Search .................. None
See application file for complete search history.

(56) References Cited

OTHER PUBLICATIONS

Ausili et al. "Two-dimensional IR correlation spectroscopy of mutants of the B-Glcosidase from the hyperthermophilic archaeon Sulfolobus solfataricus identifies the mechanism of quaternary structure stabilization and unravels the sequence of thermal unfolding events." 2004. Biochem. J. vol. 384, pp. 69-78.*
Berthomieu et al. "Effect of 13c-, 18o- and 2h-labeling on the infrared modes of UV-induced phenoxyl radicals". 1998. Biochimica et Biophysica Acta, vol. 1365, pp. 112-116.*
Dominguez-Vidal et al. "Detection of albumin unfolding preceding proteolysis using fourier transform infrared spectroscopy and chemometric data analysis". 2006. Anal. Chem. vol. 78, pp. 3257-3264.*
Haris et al. "Potential of 13C and 15N labeling for studying protein-protein interactions using fourier transform infrared spectroscopy". 1992. Biochemistry. vol. 31, pp. 6279-6284.*
Czarnik-Matusewicz, et al. "2DCOS and MCR-ALS as a combined tool of analysis of B-lactoglobulin CD spectra." 2006. J. Molec. Struct. vol. 799. pp. 211-220.*
Lefevre et al. "Study of Protein Aggregation Using Two-Dimensional Correlation Infrared Spectroscopy and Spectral Simulations". 2004. Biopolymers. vol. 73, pp. 705-715.*
Noda et al., Editorial 2DCOS-II, Vibrational Spectroscopy, Sep. 9, 2004, p. 141-142.
Noda, Recent advancement in the field of two-dimensional correlation spectroscop, Journal of Molecular Structure, Jan. 14, 2008. p. 2-26.
Bouchard et al., Formation of insulin amyloid fibrils followed by FTIR simultaneously with CD and electron microscopy, Protein Science, 2000, p. 1960-1967.
Iloro et al., Methionine Adenosyltransferase Helix Structure Unfolds at lower temperatures than B-sheet: A2D-IR-Study, Biophysical Journal, Jun. 2004, vol. 86, p. 3951-3958.

(Continued)

*Primary Examiner* — Yelena G Gakh
*Assistant Examiner* — David Weisz
(74) *Attorney, Agent, or Firm* — Hoglund & Pamias, PSC; Roberto J. Rios

(57) ABSTRACT

The invention describes a method for determining aggregation in protein, peptide or peptoid formulation, without the use of probes or additives. The method uses FTIR spectroscopy combined with the two-dimensional correlation analysis (2DCOS) which allows for the determination of the presence of aggregates, the determination of the mechanism of aggregation, allowing for correction in the pipeline manufacturing process of the protein to once again generate viable protein. In addition, the thermal transition of the protein can also be determined and a 2DCOS plot generated to compare with the established viable protein, allowing for quality control, stability and viability of the desired protein product. The ease of sample preparation and data analysis allows for the automation of this method.

11 Claims, 15 Drawing Sheets

OTHER PUBLICATIONS

Fulara et al., De novo Refolding and Aggregation of Insulin in a Nonaqueous Environment: An Inside out Protein Remake, J. Phys. Chem. B, 2008, 112, p. 8744-8747.

Natalello et al., Conformational plasticity of the Gerstmann-Sträussler-Scheinker disease peptide as indicated by its multiple aggregation pathways, J. Mol. Biol., 2008, 1349-61.

Carpenter, Receptors for Epidermal Growth Factor and Other Polypeptide Mitogens, Ann.Rev. Biochem, 1987, 881-914.

Noda, Advances in two-dimensional correlation spectroscopy, Vibrational Spectroscopy 36, 2004, p. 143-165.

Noda et al., Generalized Two-Dimensional Correlation Spectroscopy, Focal Point, vol. 54, No. 7, 2000, p. 236A-248A.

Radovan et al., Effect of pressure on islet amyloid polypeptide aggregation: revealing the polymorphic nature of the fibrillation process, Biochemistry 47, 2008, p. 6352-60.

Murray et al., Amyloid B Protein: AB40 Inhibits AB42 Oligomerization, J. Am. Chem. Soc., 2009, 131, p. 6316-17.

Li et al., Application of vibrational spectroscopy to the structural characterization of monoclonal antibody and its aggregate, Cur.Phar.Biotech, 2009, p. 391-9.

Arrondo et al, Structure and dynamics of membrane proteins as studied by infrared spectroscopy, Prog.Biophy.Mol.Biol. 72, 1999, p. 367-405.

Oh et al., Beta-azidoalanine as an IR probe: application to amyloid Abeta(16-22) aggregation, J.Phys.Chem.B, 2008, 112(33), 10352-7.

Martin et al, Attenuated total reflection IR spectroscopy as a tool to investigate the orientation and tertiary structure changes in fusion proteins, Bioch, 2003, 97-103.

Dongmei et al, Effect of Methionine Oxidation on the Structural Properties, Conformational Stability, and Aggregation of Immunoglobulin Light Chain LEN†, BioChem, 2008, 47, 8665-77.

Vigano et al, Attenuated Total Reflection IR Spectroscopy as a Tool to Investigate the Structure, Orientation, and Tertiary Structure Changes . . . , Biopoly, 2000, V.55, p. 373-380.

Tatulian, Attenuated Total Reflection Fourier Transform Infrared Spectroscopy: A Method of Choice for Studying Membrane Proteins and Lipids†, Biochem, 2003, 42, 11898-11907.

Petty et al, Intersheet rearrangement of polypeptides during nucleation of B-sheet aggregates, PNAS, 2005, vol. 102, No. 40, p. 14272-14277.

Dobson, The structural basis of protein folding and its links with human disease, Phyl.Trans.R.Soc.Lond.B, 2001, 356, p. 133-145.

Pastrana et al, Centrim: Its Secondary Structure in the Presence and Absence of Cations, Biochem 2002, 41, p. 6911-6919.

Ortiz et al, Dynamics of Hydrogen-Deuterium Exchange in Chlamydomonas Centrin, Biochem 2005, 44, p. 2409-2418.

Montelione et al, Solution Structure of Murine Epidermal Growth Factor Determined by NMR Spectroscopy and Refined by Energy Minimization with Restraints, Biochem, 1992, 31, 236-249.

* cited by examiner

FIG. 6

| spectrum | temperature °C | wavenumber nm (β-turn) aggreg | intensity | fraction* | wavenumber nm rc | intensity | fraction | wavenumber nm β-sheet | intensity | fraction | wavenumber nm Arg-aggreg | intensity | fraction | wavenumber nm Tyr | intensity | fraction |
|---|---|---|---|---|---|---|---|---|---|---|---|---|---|---|---|---|
| 1 | 2.9 | 1685.57 | 0.064 | | 1643.15 | 0.222 | | 1624.61 | 0.154 | | 1613.00 | 0.105 | | 1514.64 | 0.023 | |
| 2 | 5.8 | 1685.57 | 0.062 | | 1643.15 | 0.222 | | 1624.61 | 0.155 | | 1613.11 | 0.106 | | 1514.64 | 0.023 | |
| 3 | 9.3 | 1685.57 | 0.062 | | 1643.15 | 0.227 | 1.00 | 1624.61 | 0.159 | | 1613.98 | 0.116 | 1.00 | 1514.64 | 0.023 | 1.00 |
| 4 | 12.9 | 1685.57 | 0.065 | 1.00 | 1643.15 | 0.226 | 1.00 | 1624.61 | 0.164 | 1.00 | 1613.98 | 0.113 | 0.97 | 1514.64 | 0.023 | 1.00 |
| 5 | 16.6 | 1685.57 | 0.065 | 1.00 | 1643.15 | 0.225 | 0.99 | 1624.61 | 0.161 | 0.98 | 1613.98 | 0.112 | 0.97 | 1514.64 | 0.022 | 0.96 |
| 6 | 20.5 | 1685.57 | 0.065 | 1.00 | 1643.15 | 0.224 | 0.99 | 1624.61 | 0.159 | 0.97 | 1614.07 | 0.107 | 0.92 | 1514.29 | 0.022 | 0.96 |
| 7 | 24.0 | 1685.57 | 0.065 | 1.00 | 1643.15 | 0.224 | 0.99 | 1624.61 | 0.154 | 0.94 | 1614.62 | 0.106 | 0.91 | 1514.11 | 0.022 | 0.94 |
| 8 | 28.0 | 1685.57 | 0.065 | 1.00 | 1643.15 | 0.224 | 0.99 | 1624.61 | 0.154 | 0.94 | 1614.87 | 0.106 | 0.91 | 1514.11 | 0.022 | 0.94 |
| 9 | 31.6 | 1685.57 | 0.065 | 1.00 | 1644.98 | 0.222 | 0.98 | 1624.61 | 0.154 | 0.94 | 1615.12 | 0.106 | 0.91 | 1514.03 | 0.021 | 0.92 |
| 10 | 35.3 | 1685.57 | 0.062 | 0.95 | 1644.98 | 0.219 | 0.96 | 1624.61 | 0.015 | 0.09 | 1615.12 | 0.106 | 0.91 | 1514.00 | 0.020 | 0.88 |
| 11 | 39.1 | 1685.57 | 0.062 | 0.95 | 1644.98 | 0.219 | 0.96 | 1624.61 | 0.147 | 0.90 | 1615.12 | 0.105 | 0.91 | 1513.90 | 0.020 | 0.87 |
| 12 | 42.9 | 1685.57 | 0.062 | 0.95 | 1644.98 | 0.217 | 0.96 | 1624.61 | 0.145 | 0.88 | 1615.12 | 0.103 | 0.89 | 1513.90 | 0.020 | 0.86 |
| 13 | 46.7 | 1685.57 | 0.062 | 0.95 | 1644.98 | 0.216 | 0.95 | 1624.61 | 0.138 | 0.84 | 1615.12 | 0.101 | 0.87 | 1513.85 | 0.020 | 0.86 |
| 14 | 50.5 | 1685.57 | 0.062 | 0.95 | 1644.98 | 0.213 | 0.94 | 1624.61 | 0.138 | 0.84 | 1615.12 | 0.099 | 0.85 | 1513.85 | 0.019 | 0.85 |
| 15 | 54.1 | 1685.57 | 0.062 | 0.95 | 1642.40 | 0.192 | 0.85 | 1624.61 | 0.137 | 0.84 | 1615.12 | 0.098 | 0.84 | 1513.44 | 0.019 | 0.84 |
| 16 | 57.6 | 1685.57 | 0.062 | 0.95 | 1642.40 | 0.179 | 0.79 | 1624.61 | 0.133 | 0.81 | 1615.12 | 0.092 | 0.79 | 1513.40 | 0.019 | 0.83 |
| 17 | 61.2 | 1685.57 | 0.059 | 0.85 | 1642.40 | 0.170 | 0.75 | 1624.61 | 0.126 | 0.77 | 1615.12 | 0.090 | 0.78 | 1513.37 | 0.018 | 0.81 |
| 18 | 64.8 | 1685.57 | 0.055 | 0.85 | 1642.40 | 0.161 | 0.71 | 1624.61 | 0.124 | 0.76 | 1615.12 | 0.090 | 0.78 | 1513.34 | 0.018 | 0.80 |
| 19 | 68.2 | 1685.57 | 0.055 | 0.85 | 1642.40 | 0.157 | 0.69 | 1624.61 | 0.120 | 0.73 | 1615.12 | 0.089 | 0.77 | 1513.34 | 0.018 | 0.77 |
| 20 | 71.6 | 1685.57 | 0.055 | 0.85 | 1642.40 | 0.154 | 0.68 | 1624.61 | 0.119 | 0.73 | 1615.12 | 0.089 | 0.77 | 1513.34 | 0.017 | 0.76 |
| 21 | 74.7 | 1685.57 | 0.054 | 0.90 | 1642.40 | 0.149 | 0.66 | 1624.61 | 0.119 | 0.73 | 1615.12 | 0.091 | 0.78 | 1512.90 | 0.017 | 0.75 |
| 22 | 77.9 | 1685.57 | 0.055 | 0.92 | 1642.40 | 0.148 | 0.65 | 1624.61 | 0.119 | 0.73 | 1615.12 | 0.097 | 0.84 | 1512.90 | 0.017 | 0.73 |
| 23 | 80.9 | 1685.57 | 0.057 | 0.95 | 1642.40 | 0.143 | 0.63 | 1624.61 | 0.119 | 0.73 | 1615.12 | 0.102 | 0.88 | 1512.82 | 0.016 | 0.71 |
| 24 | 84.2 | 1685.57 | 0.057 | 0.95 | 1642.40 | 0.138 | 0.61 | 1624.61 | 0.119 | 0.73 | 1615.12 | 0.105 | 0.91 | 1512.82 | 0.016 | 0.71 |
| 25 | 87.1 | 1685.57 | 0.060 | 1.00 | 1642.40 | 0.135 | 0.59 | 1624.61 | 0.119 | 0.73 | 1615.12 | 0.105 | | 1512.82 | 0.016 | 0.71 |

FIG. 15

| spectrum | temperature °C | wavenumber nm MLT rc | intensity | fraction* | wavenumber nm MLT α-helix | intensity | fraction | wavenumber nm 13C-Ccen rc/MLT aggreg | intensity | fraction |
|---|---|---|---|---|---|---|---|---|---|---|
| 1 | 1.8 | 1673.77 | 0.431 | | 1645.50 | 0.349 | | | 0.289 | |
| 2 | 5.9 | 1673.77 | 0.431 | | 1645.50 | 0.351 | | | 0.294 | |
| 3 | 6.2 | 1673.77 | 0.431 | | 1645.50 | 0.355 | | | 0.298 | |
| 4 | 10.1 | 1673.77 | 0.432 | | 1645.50 | 0.359 | | | 0.303 | |
| 5 | 15.1 | 1674.16 | 0.432 | | 1645.50 | 0.360 | | | 0.307 | |
| 6 | 20.1 | 1674.16 | 0.432 | | 1645.50 | 0.360 | | | 0.308 | |
| 7 | 25.1 | 1674.16 | 0.432 | | 1645.50 | 0.364 | | | 0.312 | |
| 8 | 29.9 | 1674.16 | 0.434 | 1.00 | 1645.50 | 0.366 | 1.00 | 1618.80 | 0.314 | 0.73 |
| 9 | 34.5 | 1674.16 | 0.431 | 0.99 | 1645.50 | 0.366 | 1.00 | 1618.80 | 0.316 | 0.73 |
| 10 | 39.5 | 1675.34 | 0.429 | 0.99 | 1645.50 | 0.360 | 0.98 | 1618.80 | 0.325 | 0.75 |
| 11 | 44.2 | 1675.27 | 0.423 | 0.97 | 1645.50 | 0.344 | 0.94 | 1618.80 | 0.349 | 0.81 |
| 12 | 49.5 | 1675.8 | 0.422 | 0.97 | 1645.50 | 0.319 | 0.87 | 1619.00 | 0.362 | 0.84 |
| 13 | 54.0 | 1675.8 | 0.421 | 0.97 | 1645.50 | 0.311 | 0.85 | 1619.19 | 0.376 | 0.87 |
| 14 | 59.0 | 1676.15 | 0.418 | 0.96 | 1645.50 | 0.307 | 0.84 | 1619.19 | 0.381 | 0.88 |
| 15 | 63.5 | 1676.45 | 0.415 | 0.96 | 1645.50 | 0.304 | 0.83 | 1619.19 | 0.387 | 0.90 |
| 16 | 68.2 | 1676.84 | 0.414 | 0.95 | 1645.50 | 0.302 | 0.83 | 1619.19 | 0.395 | 0.92 |
| 17 | 73.5 | 1677.19 | 0.412 | 0.95 | 1645.50 | 0.301 | 0.82 | 1619.19 | 0.403 | 0.94 |
| 18 | 78.2 | 1677.36 | 0.411 | 0.95 | 1645.50 | 0.301 | 0.82 | 1619.19 | 0.408 | 0.95 |
| 19 | 83.1 | 1677.49 | 0.410 | 0.94 | 1645.50 | 0.298 | 0.81 | 1619.19 | 0.414 | 0.96 |
| 20 | 88.0 | 1677.54 | 0.409 | 0.94 | 1645.50 | 0.298 | 0.81 | 1619.19 | 0.419 | 0.97 |
| 21 | 92.4 | 1677.72 | 0.408 | 0.94 | 1645.50 | 0.295 | 0.81 | 1619.81 | 0.426 | 0.99 |
| 22 | 95.8 | 1677.85 | 0.404 | 0.93 | 1645.50 | 0.290 | 0.79 | 1620.00 | 0.431 | 1.00 |

METHOD FOR DETERMINATION OF PROTEIN, PEPTIDE OR PEPTOID AGGREGATION, STABILITY, AND VIABILITY AND SYSTEM USING THE SAME

STATEMENT REGARDING FEDERALLY SPONSORED RESEARCH OR DEVELOPMENT

This invention was made with government support under grant numbers NIH-COBRE P20 RR16439-01 (BPR), NIH-SCORE 5-S06GM08103 (BPR) awarded by the National Institute of Health (NIH). The government has certain rights in the invention.

BACKGROUND OF THE INVENTION

Proteins are large organic compounds made of amino acids arranged in a linear chain and joined together by peptide bonds between the carboxyl and amino groups of adjacent amino acid residues. The sequence of amino acids in a protein is defined by a gene and encoded in the genetic code. Although this genetic code specifies 20 "standard" amino acids plus selenocysteine and—in certain archaea—pyrrolysine, the residues in a protein are sometimes chemically altered by post-translational modification: either before the protein can function in the cell, or as part of control mechanisms. Proteins can also work together to achieve a particular function, and they often associate to form stable complexes. Like other biological macromolecules such as polysaccharides and nucleic acids, proteins are essential parts of organisms and participate in every process within cells. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. Proteins are also necessary in animals' diets, since animals cannot synthesize all the amino acids they need and must obtain essential amino acids from food. Through the process of digestion, animals break down ingested protein into free amino acids that are then used in metabolism.

Proteins are linear polymers built from 20 different L-α-amino acids. All amino acids possess common structural features, including an α carbon to which an amino group, a carboxyl group, and a variable side chain are bonded. The side chains of the standard amino acids have different chemical properties that produce three-dimensional protein structure and are therefore critical to protein function. The amino acids in a polypeptide chain are linked by peptide bonds formed in a dehydration reaction. Once linked in the protein chain, an individual amino acid is called a residue, and the linked series of carbon, nitrogen, and oxygen atoms are known as the main chain or protein backbone. The peptide bond has two resonance forms that contribute some double-bond character and inhibit rotation around its axis, so that the alpha carbons are roughly coplanar. The other two dihedral angles in the peptide bond determine the local shape assumed by the protein backbone. Due to the chemical structure of the individual amino acids, the protein chain has directionality. The end of the protein with a free carboxyl group is known as the C-terminus or carboxy terminus, whereas the end with a free amino group is known as the N-terminus or amino terminus.

Proteins are assembled from amino acids using information encoded in genes. Each protein has its own unique amino acid sequence that is specified by the nucleotide sequence of the gene encoding this protein. The genetic code is a set of three-nucleotide sets called codons and each three-nucleotide combination stands for an amino acid, for example AUG stands for methionine. Because DNA contains four nucleotides, the total number of possible codons is 64; hence, there is some redundancy in the genetic code, with some amino acids specified by more than one codon. Genes encoded in DNA are first transcribed into pre-messenger RNA (mRNA) by proteins such as RNA polymerase. Most organisms then process the pre-mRNA (also known as a primary transcript) using various forms of post-transcriptional modification to form the mature mRNA, which is then used as a template for protein synthesis by the ribosome.

The process of synthesizing a protein from an mRNA template is known as translation. The mRNA is loaded onto the ribosome and is read three nucleotides at a time by matching each codon to its base pairing anticodon located on a transfer RNA molecule, which carries the amino acid corresponding to the codon it recognizes. The enzyme aminoacyl tRNA synthetase "charges" the tRNA molecules with the correct amino acids. The growing polypeptide is often termed the nascent chain. Proteins are always biosynthesized from N-terminus to C-terminus. The size of a synthesized protein can be measured by the number of amino acids it contains and by its total molecular mass.

Most proteins fold into unique 3-dimensional structures. The shape into which a protein naturally folds is known as its native state. Although many proteins can fold unassisted, simply through the chemical properties of their amino acids, others require the aid of molecular chaperones to fold into their native states. There are four distinct aspects of a protein's structure:

Primary structure: the amino acid sequence

Secondary structure: regularly repeating local structures stabilized by hydrogen bonds. Because secondary structures are local, many regions of different secondary structure can be present in the same protein molecule.

Tertiary structure: the overall shape of a single protein molecule; the spatial relationship of the secondary structures to one another.

Quaternary structure: the shape or structure that results from the interaction of more than one protein molecule, usually called protein subunits in this context, which function as part of the larger assembly or protein complex.

Proteins are not entirely rigid molecules. In addition to these levels of structure, proteins may shift between several related structures while they perform their biological function. In the context of these functional rearrangements, these tertiary or quaternary structures are usually referred to as "conformations," and transitions between them are called conformational changes.

Protein aggregation is characterized as a misfolded, rigid protein grouping which is considered a prevalent phenomenon throughout the industrial bioprocess. Aggregation is considered a primary mode of protein degradation, often leading to immunogenicity of the protein and a loss of bioactivity. Protein aggregation is of critical importance in a wide variety of biomedical situations, ranging from abnormal disease states, such as Alzheimer's and Parkinson's disease, to the production, stability and delivery of protein drugs. As shown in FIG. 1, protein aggregation, which could be amorphous or fibrillar in nature, starts by one of two different mechanisms: A) self-aggregation, in which the partially-folded intermediates are the immediate precursors for aggregation, and B) hetero-aggregation, in which the aggregation of one protein is mediated by another protein.

The formation of protein aggregates is critical in industrial applications, because it can highly affect the production of protein-based drugs or commercial enzymes, greatly lowering the production yields. That is why the detection and determination of protein aggregates is a key point in the biopharmaceutical industry, as well as, in scientific research. Several methods (some of them patented) have been proposed in the past for the determination of aggregates in mixtures. These prior art methods are either designed for a particular protein or peptide and/or require the addition of a foreign probe and thus, does not represent a generalized method with a universal application to a class of biological molecules. Several spectroscopic techniques have been used, like UV-Vis spectroscopy with the aid of probes, fluorescence also using internal or exogenous probes, similarly near UV circular dichroism (CD), limiting the detection of the aggregate to its immediate vicinity; nuclear magnetic resonance (NMR) could be used to detect protein aggregation by the appearance of band broadening. Sedimentation analysis could also be used to identify the extent of oligomerization as long as the protein of interest has a large enough molar extinction coefficient. Chromatographic techniques such as size exclusion could also detect the presence of protein aggregates. But these techniques may require the use of exogenous probes, large amounts of protein, are time consuming and none allow for the determination of the mechanism of aggregation.

SUMMARY OF THE INVENTION

The invention provides a method for determining aggregation in protein, peptide or peptoid formulation, in solution or lyophilized state without the use of probes or additives.

According to an aspect of the invention, the protein sample is spectroscopically analyzed and the spectral data analyzed using the established method to determine viability of the protein sample. The method can be fully automated and be used for the determination of the mechanism of aggregation.

According to another aspect of the invention, the method has been applied to membrane proteins, hydrophilic proteins, peptides and peptoids as a single component or in binary or ternary mixtures with other peptides or lipid mixtures. When in mixtures, one of the components must be isotopically labeled to allow for the simultaneous detection of each component.

One advantageous aspect of the invention lies on the flexibility of the sample preparation, its potential for automation and data analysis which have proven its utility for pharmaceutical protein formulation.

In another aspect of the invention, the method can be applied to any protein, peptide or peptoid sample in several environments, aqueous or lipidic. The method can be used qualitatively and/or quantitatively for determining protein aggregation. Data analysis is performed through which the mechanism of protein aggregation is determined and the stability and/or viability of said protein, peptide or peptoid can be determined.

According to one aspect of the invention, the method involves transmission Fourier transform infrared (FT-IR) and/or attenuated total reflectance (ATR) FT-IR spectroscopy and two-dimensional correlation spectroscopy (2DCOS) for the analysis of these proteins, peptides or peptoids. The graphical treatment provides greater resolution of broad bands, as is the case of the amide I band observed for proteins, peptides and peptoids. Standard manipulative operations used in 2D correlation, such as Hilbert transformation, Gram-Schmidt orthogonalization and asynchronous correlation can be easily comprehended as the combinations of rotations and projections of signal vectors.

These and other aspects of the invention will be better understood by reference to the Drawings, Detailed Description, and the Examples.

BRIEF DESCRIPTION OF THE DRAWINGS

A detailed description of embodiments of the invention will be made with reference to the accompanying drawings, wherein like numerals designate corresponding parts in the several figures.

FIG. 6 shows a table summarizing the changes in intensity during the thermal dependence study of EGF.

FIG. 15 shows a summary of CCcen-MLT complex thermal dependence study and MLT aggregates.

DETAILED DESCRIPTION OF THE INVENTION

Figure 1:
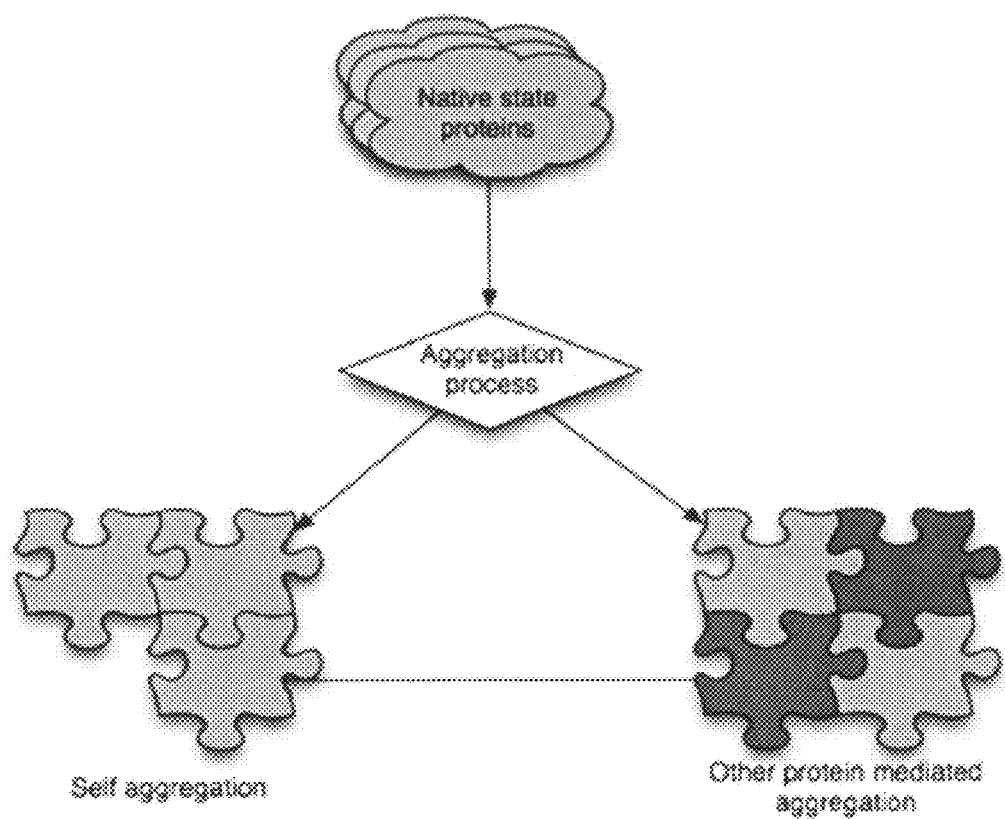
FIG. 1 shows a diagram of the typical protein aggregation mechanism.
Figure 2:
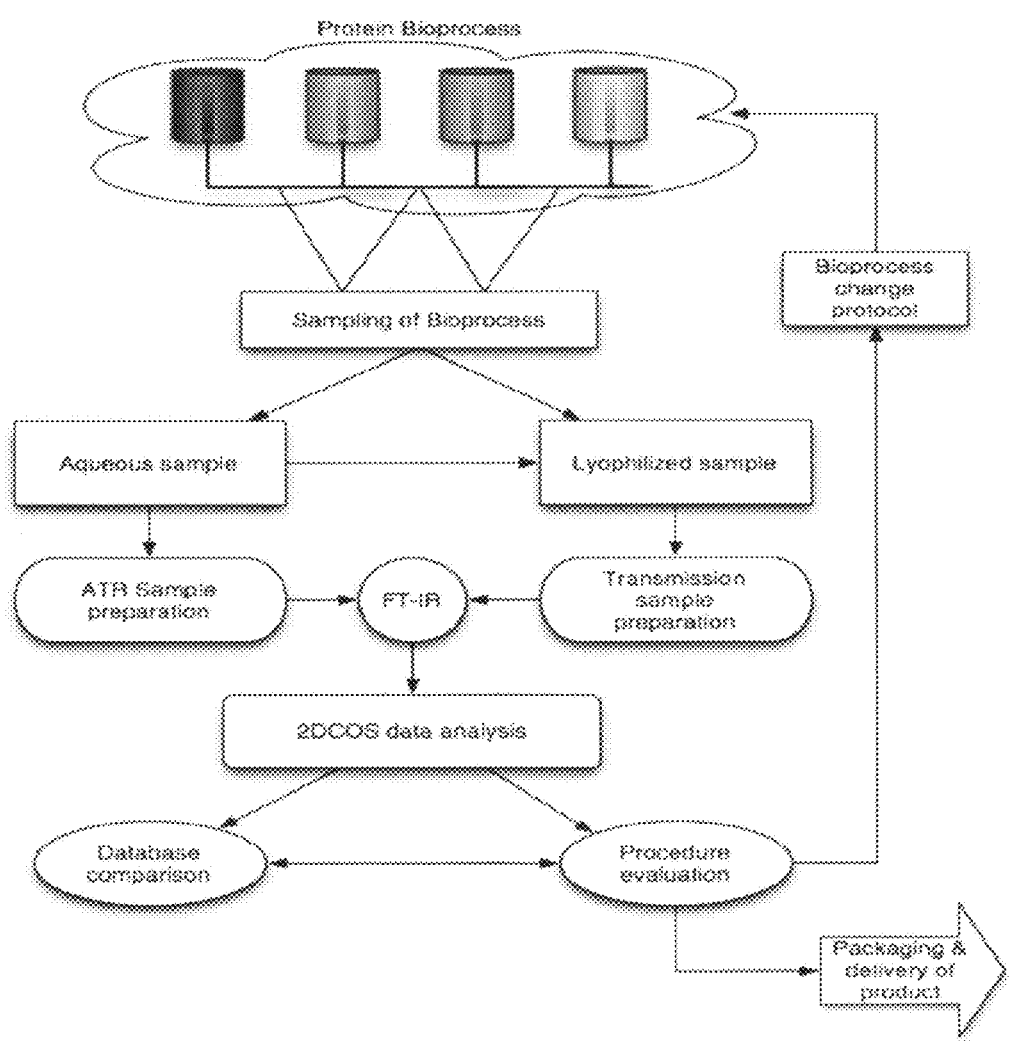
FIG. 2 shows flowchart indicating the different phases of the method according to one aspect of the invention.

A preferred embodiment of the invention will be explained in accordance to FIG. 2. During a bioprocess, samples from different parts of the bioprocess, which could be aqueous or lyophilized, are monitored by Fourier Transform Infrared (ATR or transmission) spectroscopy (FT-IR) and analyzed using two-dimensional correlation spectroscopy (2DCOS) in order to search for aggregates. If aggregates are found, an evaluation procedure that might include comparing the results against an established database can be started and as a result the protocol used in the bioprocess can be modified or changed. FT-IR spectroscopy allows for a high degree of flexibility and speed in the determination of protein aggregates, with limited manipulation, and without the use of exogenous probes. The method described according to the invention uses FT-IR spectroscopy combined with the two-dimensional correlation analysis (2DCOS) which allows for the determination of the presence of aggregates, the determination of the mechanism of aggregation, allowing for correction in the pipeline manufacturing process of the protein to once again generate viable protein. In addition, the thermal transition of the protein can also be determined and a 2DCOS plot generated to compare with the established viable protein, allowing for quality control, stability and viability of the desired protein product. Furthermore, the ease of sample preparation and data analysis allows for the automation of this method.

FT-IR spectroscopy is sensitive to conformational changes and aggregation. This technique allows for qualitative and quantitative analysis of the extent of protein, peptide and peptoid aggregation. The use of 2DCOS allows for further analysis and provides mechanistic information related to the aggregation process. The present invention will be better understood through several examples that are not intended to be limiting. All the examples include one or all techniques as explained below.

Transmission FT-IR Spectroscopy

Sample preparation involved the use of approximately 0.5-2 mg of pure protein, peptide or peptoid, in the appropriate buffer. It was lyophilized and re-suspended in 25 μL of $D_2O$. The protein solution is applied between two custom milled $CaF_2$ windows (50×4 mm with a fixed path length of 40 μm) and sealed to prevent solvent evaporation. The cells are then set in a custom dual chamber cell holder. A similar procedure is used for the reference cell using the appropriate buffer (PBS or Hepes). A temperature probe located in close contact with the cell is used to register the temperature of the sample cell. A temperature gradient of 1° C./min is used and the acquired spectral data is received automatically through a thermocouple interface. For these experiments an FT-IR Mattson Infinity Series spectrophotometer or a Nicolet Magna 550 equipped with HgCdTe (MCT) detector was used. Typically, 256 or 305 scans are acquired for sample and for reference by using a shuttle at each temperature the spectral data is apodized with a triangular function to 4 $cm^{-1}$ and encoded to 2 $cm^{-1}$ resolution. During the spectral analysis the full width at half height (FWHH) of the amide I band can be determined as a function of temperature to establish the transition temperature.

Attenuated Total Reflectance (ATR) FT-IR Spectroscopy

This technique is frequently used for hydrogen/deuterium exchange studies, titration experiments and the determination of the orientation of reconstituted membrane proteins. In this method the protein has been fully exchanged by repeated lyophillization and redissolving the sample in $D_2O$. The fully exchanged protein sample and buffer can be spread as a film independently where the buffer is considered as the reference. For these experiments an FT-IR Mattson Infinity Series spectrophotometer equipped with an ATR accessory from Thermo Electron Corp. comprised of a horizontal ZnSe or germanium crystal with a 45° angle of incidence and HgCdTe (MCT) detector. Typically, 250 μL containing 0.5-6 mg of protein in $D_2O$ is spread unto the ATR crystal and allowed to dry, using a dry air purge. The subsequent spectrum would be representative of the protein sample and if present, the aggregated form of the protein (1620 $cm^{-1}$).

Two-Dimensional Correlation Analysis (2DCOS)

This technique is used to resolve complex bands, such as the amide I band. The protein sample is perturbed (thermally, chemically, pressure, or acoustics) inducing a dynamic fluctuation in the vibrational spectrum. The spectral data acquired by transmission FT-IR or attenuated total reflectance (ATR) FT-IR has been used in this method to determine the existence of the aggregated form of the protein, peptide or peptoid. For this, the first spectrum is subtracted from the subsequent spectra to generate the dynamic spectra. This spectral data is fast Fourier transformed (FFT) to generate the complex matrix from which an intensity matrix is obtained through the cross correlation product the synchronous and asynchronous plots are generated. The synchronous plot represents the intensity changes that occur during the perturbation. On the diagonal of this plot are the peaks or bands (known as autopeaks) that changed throughout the spectrum. Off the diagonal are the cross peaks which show the correlation between the autopeaks, that is, the relationship between the secondary structure changes observed. The asynchronous plot contains only cross peaks which are used to determine the order of events and thus the mechanism of aggregation of the protein.

| Synchronous correlation spectrum | Asynchronous correlation spectrum |
|---|---|
| Autopeaks at diagonal positions represent the extent of perturbation-induced dynamic fluctuations of spectral signals. | Cross peaks develop only if the intensity varies out of phase with each other for some Fourier frequency components of signal fluctuations. |
| Cross peaks represent simultaneous changes of spectral signals at two different wavenumbers, suggesting a coupled or related origin of intensity variations. | The sign of a cross peak is positive if the intensity change at wavenumber $v_1$ occurs before wavenumber $v_2$. The sign of a cross peak is negative if the intensity change at wavenumber $v_1$ occurs after wavenumber $v_2$. |
| If the sign of a cross peak is positive, the intensities at corresponding wavenumbers are increasing or decreasing together. If the sign is negative, one is increasing, while the other is decreasing. | The above sign rules are reversed if the same asynchronous cross peak position translated to the synchronous plot falls in a negative region ($\Phi(v_1, v_2) < 0$) |

EXAMPLE 1

Epidermal Growth Factor (EGF)

The first example chosen is a human recombinant mitogenic polypeptide, known as epidermal growth factor (EGF) comprised of amino acids and three disulfide bridges. Its secondary structure is highly conserved primarily beta sheet, turns and random coil. The cellular pathways associated to the binding of these growth-factor polypeptides to growth factor receptors lead to cell proliferation and act in an atypical manner in tumor cells.

Figure 3:
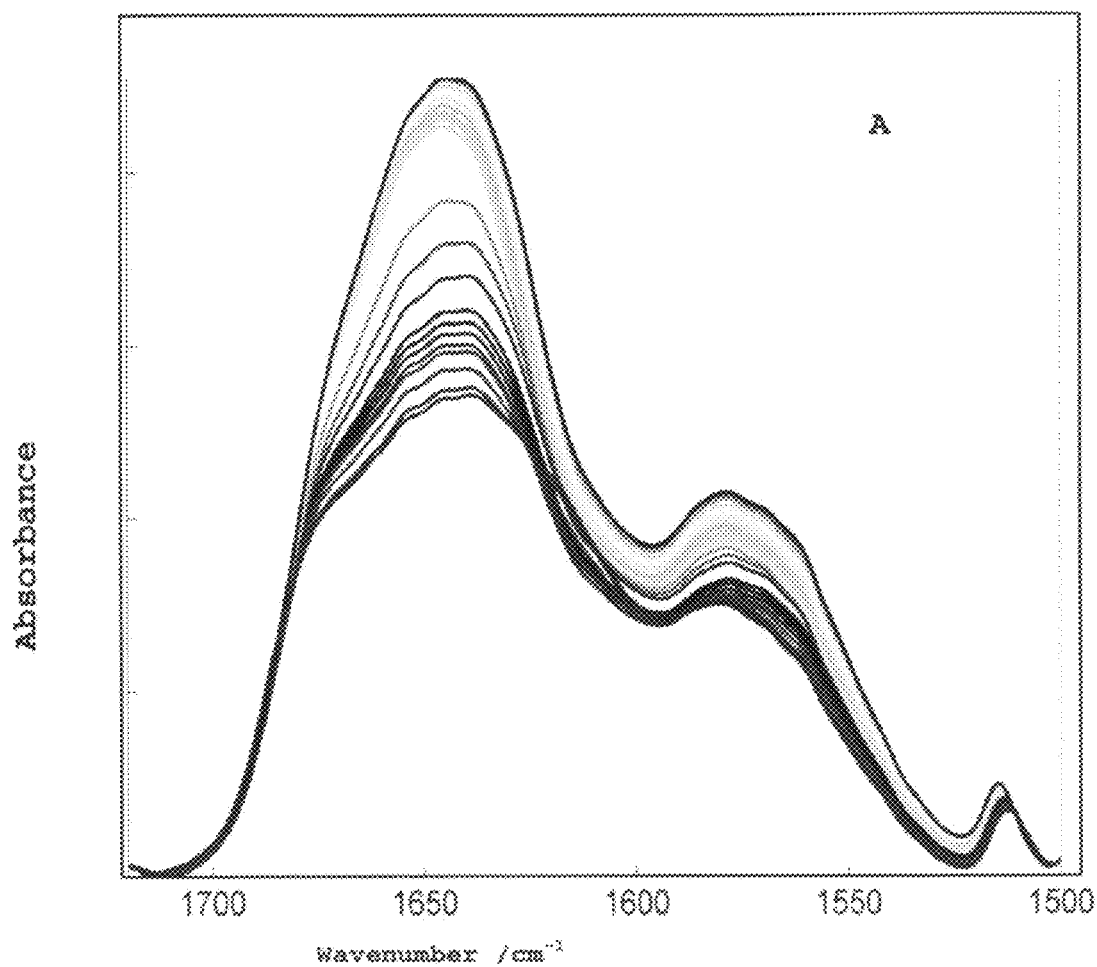
FIG. 3 shows a graph of overlaid spectra of EGF as a function of temperature in the spectral region of 1720-1500 $cm^{-1}$.
Figure 4:
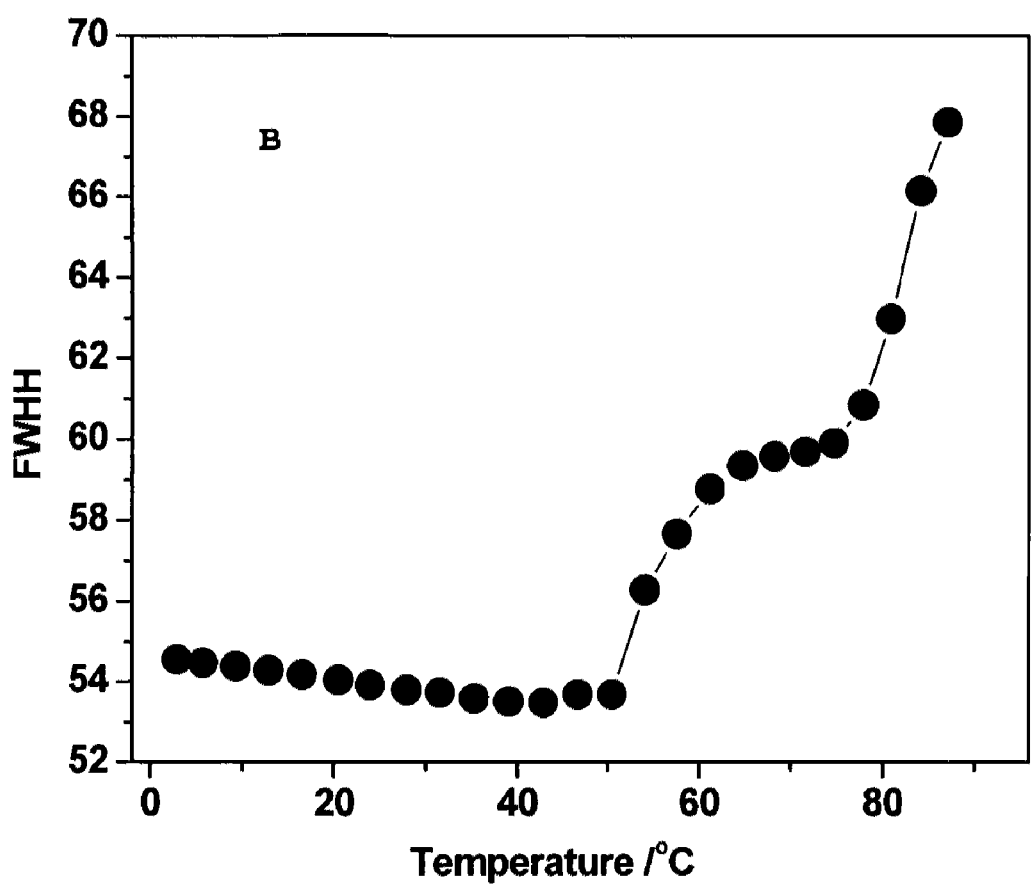
FIG. 4 shows a graph of full width at half height (FWHH) of the amide I' band as a function of temperature.
Figure 5:
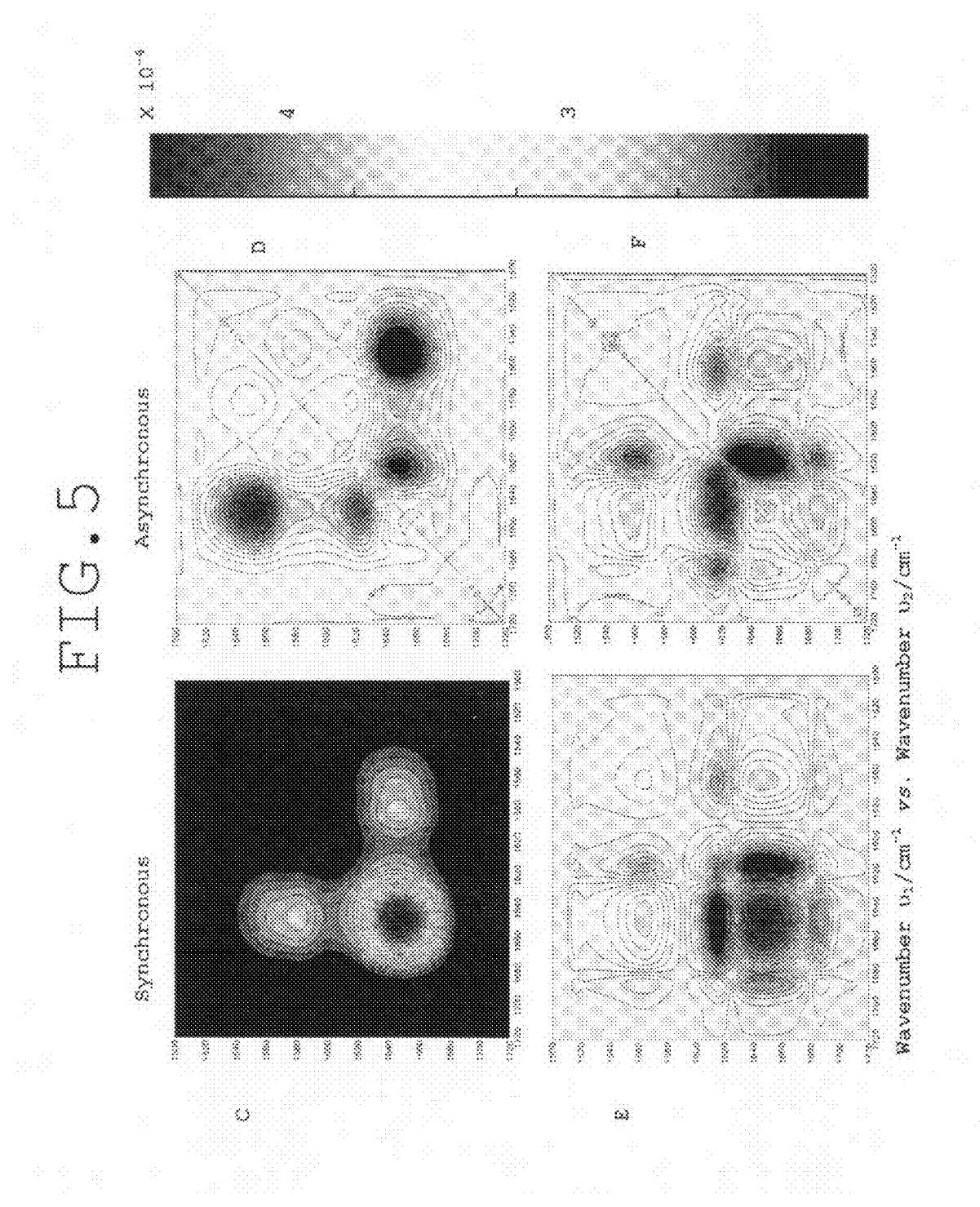
FIG. 5 shows synchronous and asynchronous 2DCOS plots for spectra collected in the temperature ranges of 2-75° C. and of 75-87° C.

Results of the thermal dependence studies for EGF within the spectral region of 1720-1500 $cm^{-1}$ are shown in FIG. 3. The decrease in intensity of the amide I band along with a shift to lower wavenumbers from 1645 to 1638 $cm^{-1}$ and the appearance of a shoulder at 1620 $cm^{-1}$ is indicative of thermal denaturation and aggregation, decrease of the amide II band associated with side chain modes. Therefore the method serves to determine the melting temperature (Tm) of the polypeptide as well. A plot of the FWHH of the amide I' band vs temperature is shown in FIG. 4. A pre-transition is observed at 58° C. with a continued increase in FWHH at approximately 83° C. is indicative of the aggregated species. FIG. 5 shows the 2DCOS plots for the temperature range of 2-75° C. and the 2DCOS plots for the temperature range of 75-87° C. As described above, the Synchronous plots contain two autopeaks in plot C, one peak at 1630-1660 $cm^{-1}$ representative of the secondary structures corresponding to β-sheet, turns and random coil and a second peak at 1590-

1550 cm$^{-1}$ corresponding to the side chain modes aspartate and glutamate. Although low resolution has been achieved it is clear that in the temperature range of 2-75° C. no aggregation is present. Meanwhile, at higher temperatures 78-87° C. the synchronous plot E contains autopeaks at 1617 and 1680 cm$^{-1}$, representative of aggregation of the polypeptide. Also present in the synchronous plot E are the autopeaks associated with the secondary structure and the side chain modes. Following Noda's rule for the interpretation of the asynchronous plot to determine the order of events in plot F, the aggregation occurs after the thermal transition of the β-sheet motif.

FIG. 6 shows for EGF, a table summarizing the spectral intensities, temperature and structurally intact (unchanged) fraction of the protein domain used to determine the percent of aggregation. Typically, the 2DCOS identifies the peaks that are correlated or involved in the aggregation process. The intensities of these peaks are then listed in a Table to identify the temperature range in which a change in direction (increase or decrease in intensity) is observed. This is the temperature at which the aggregation process begins. The largest intensity is used as the maximum intensity and the last temperature intensity value is used to define the limits of the aggregation process. Thus, allowing for the quantitative determination of the aggregated protein sample.

EXAMPLE 2

Methionine Adenosyltransferase (MAT)

Figure 7:
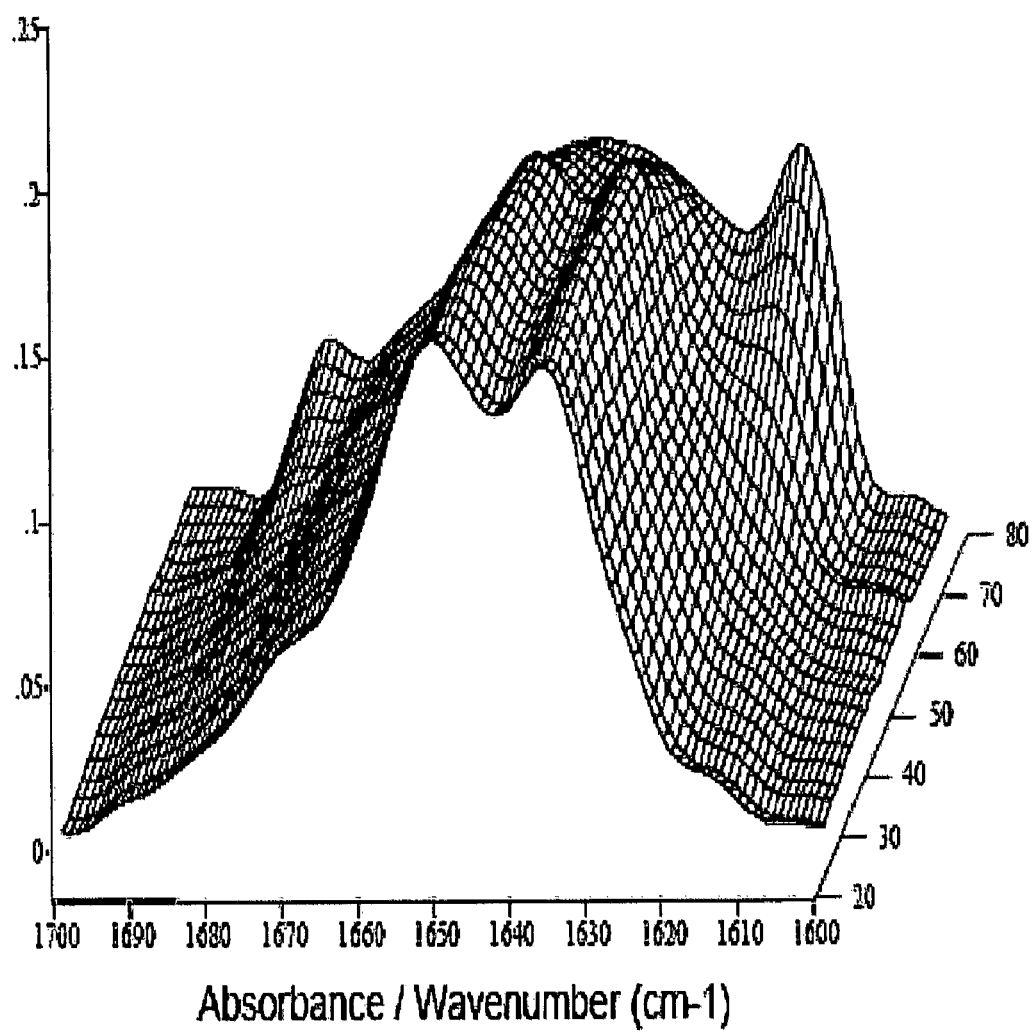
FIG. 7 is a temperature dependence 3D plot of the deconvolved amide I region in $D_2O$ in the 25-80° C. interval of MAT.

In the thermal denaturation of the MAT (Methionine adenosyltransferase) protein (1,584 amino acids in its homotetramer form, for a molecular weight of 198 kDa), apparently a cooperative two-state denaturation process is assumed, as seen at the 3D plot of the deconvolved spectra for MAT in FIG. 7. Further studies using 2DCOS show that it's not a fully two state process, with a more complex denaturation pattern. The aggregation is characterized by the appearance of two bands at 1620 cm$^{-1}$ and 1680 cm$^{-1}$.

Figure 8:
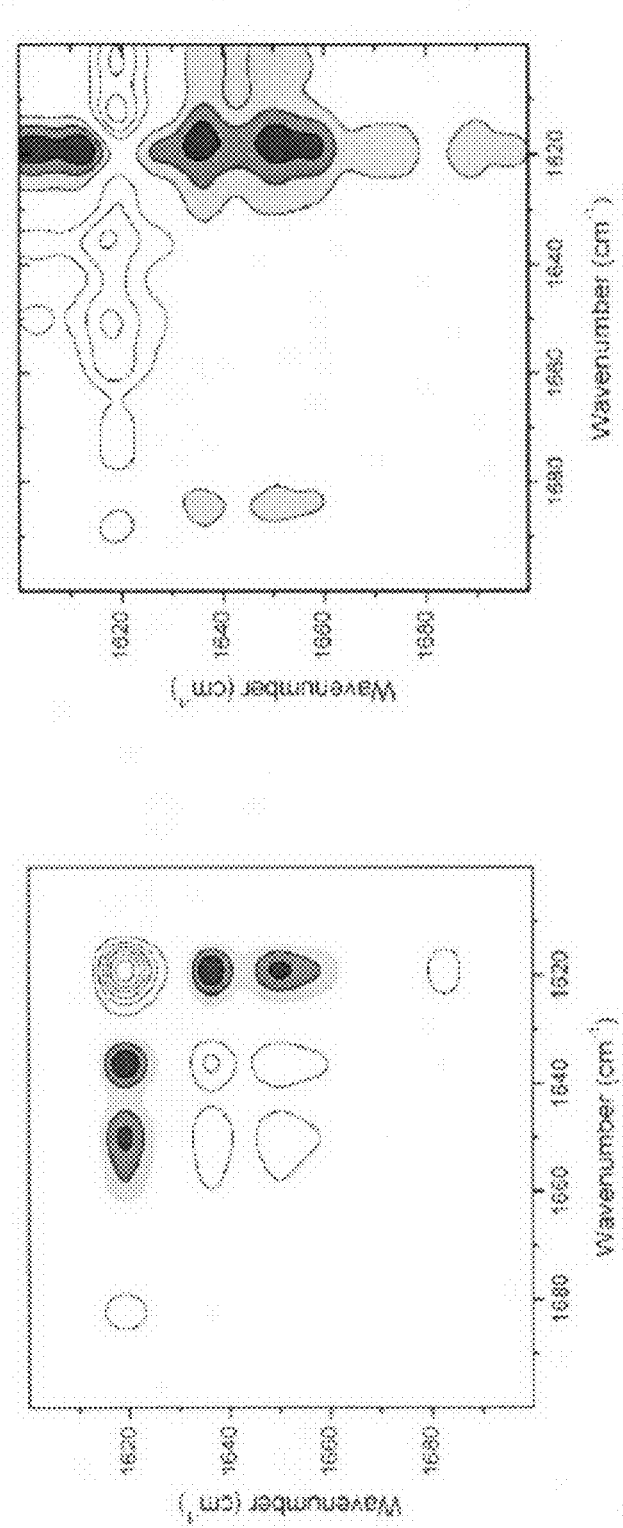
FIG. 8 shows synchronous and asynchronous correlation contour plots in the region 1700-1600 $cm^{-1}$ of MAT in the interval 37-53° C.

In the temperature range of 37-53° C., the activity of the protein is being gradually lost. 2DCOS plots as shown in FIG. 8 have been used to show that aggregation has occurred at the expense of the α-helix and β-sheet structural motifs and also of the residual β-turns. The synchronous plot has autopeaks at 1652 cm$^{-1}$ and 1635 cm$^{-1}$, with a positive cross-peak between them, showing that both structures (α-helix and β-turn, respectively) are decreasing. The most prominent band is the aggregation band, at 1620 cm$^{-1}$, coupled with its high-frequency correlated autopeak at 1680 cm$^{-1}$. The main aggregation band at 1620 cm$^{-1}$ has negative cross-peaks with the autopeaks at 1652 cm$^{-1}$ and 1635 cm$^{-1}$, showing that the aggregation is increasing with a concomitant decrease of the secondary structure associated bands.

EXAMPLE 3

Insulin

Figure 9:
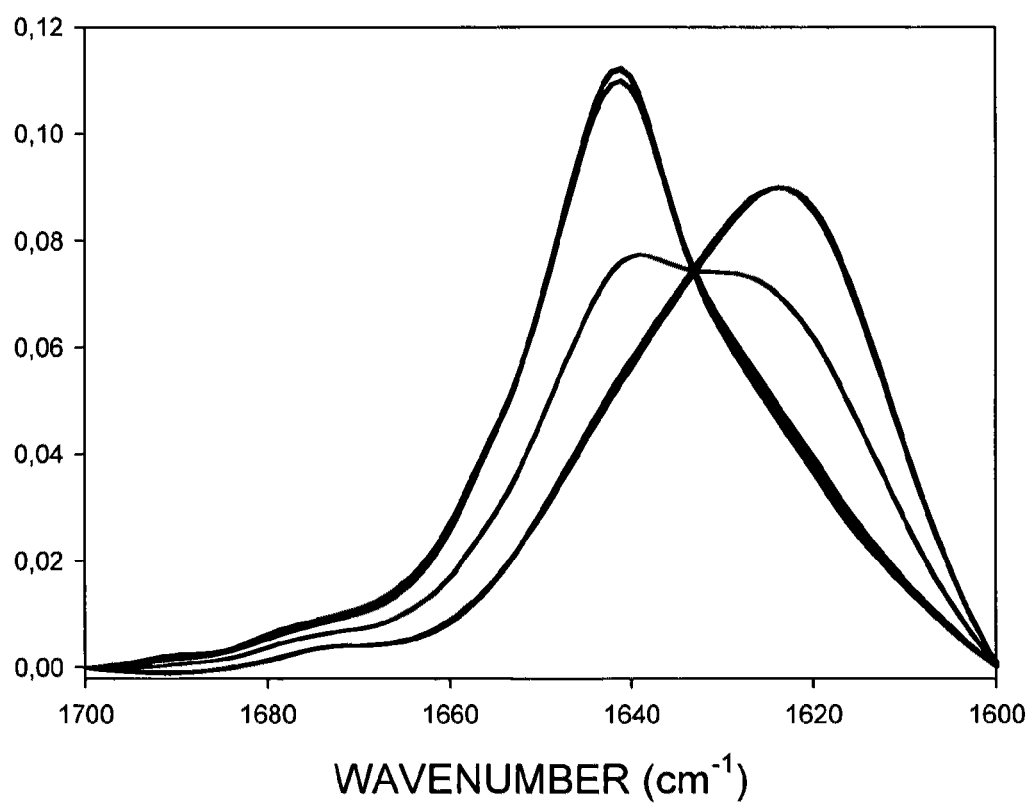
FIG. 9 shows FT-IR spectra corresponding to the heating process from 25 to 70° C.

Insulin is an α-helical peptide with a total of 51 amino acids (about 6.5 kDa). Heating this peptide up to 70° C. produces amyloid fibers, formed by β-sheet structure. FT-IR spectroscopy can be used to study this process as the appearance of a large band at 1620 cm$^{-1}$ as shown in FIG. 9, associated to fiber formation. Thus, this method is comparably easy when compare to other methods, which require preparing several samples, the use of external probes and does not analyze the secondary structure, so the mechanism of the aggregation can't be studied.

Figure 10:
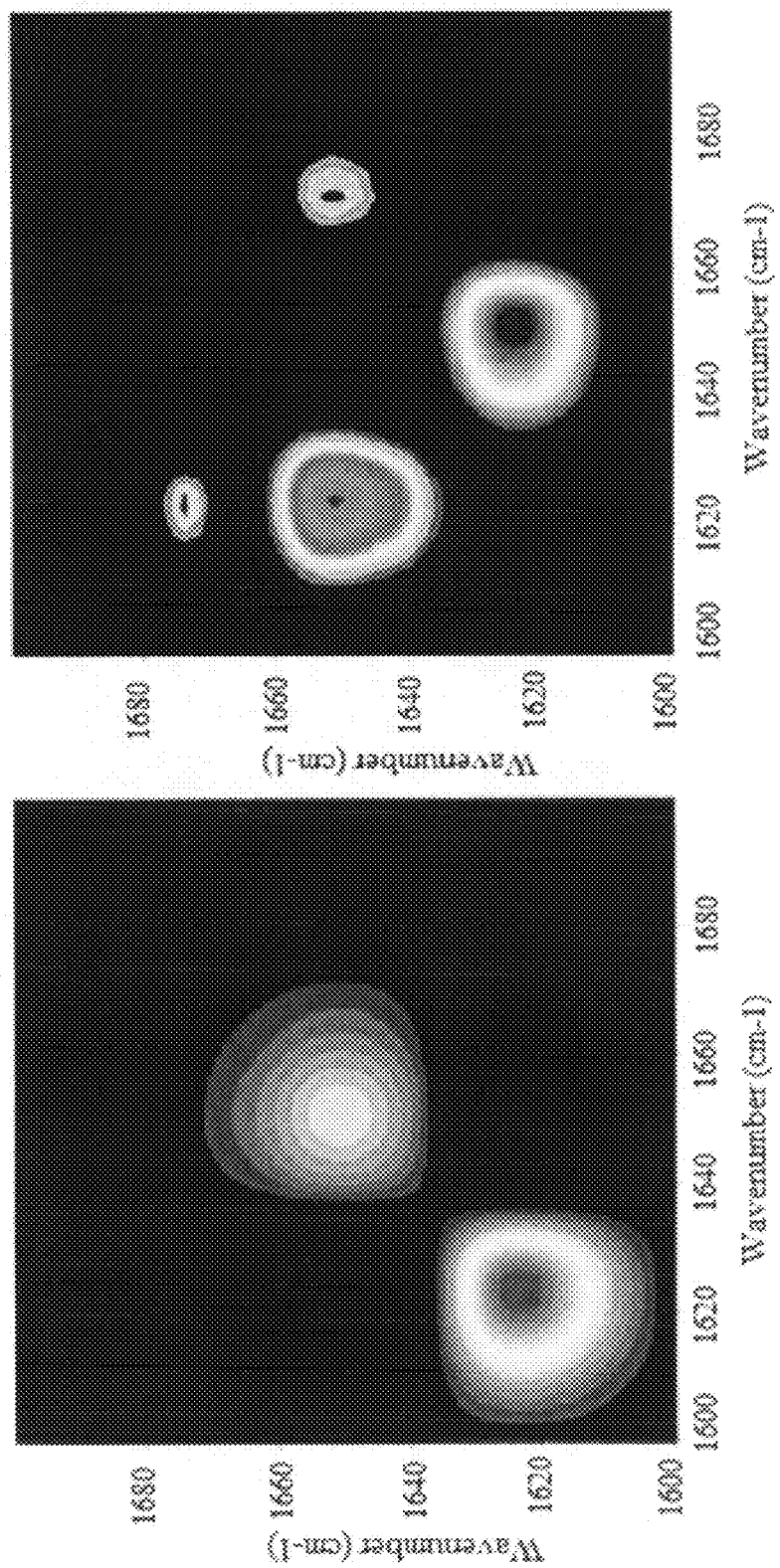
FIG. 10 shows synchronous and asynchronous correlation contour plot in the region 1700-1600 $cm^{-1}$ of insulin, in the interval 25-70° C.

FIG. 10 shows the asynchronous and synchronous plots summarizing the events related to fiber formation. An autopeak at 1620 cm$^{-1}$ on the Synchronous plot is associated to the fiber formation with the concomitant loss of the α-helix native structure (1650 cm$^1$). The asynchronous plot shows this process involving a new structure at 1670 cm$^{-1}$ (β-turns).

EXAMPLE 4

Centrin

Centrin is a calcium binding protein of 172 amino acids, M$_r$, approximately 20 kDa, belonging to the EF-hand superfamily. This highly conserved protein shares approximately 50% sequence identity with calmodulin. Centrin was extensively dialyzed to ensure desired buffer conditions. The first dialysis was against: 16 mM Hepes, 50 mM NaCl, 2.0 mM EDTA and 2.0 mM EGTA at pH 7.4. A second dialysis was carried-out against: 16 mM Hepes, mM NaCl and 1.0 mM EDTA at pH 7.4. The titration stock solutions containing 0.5 mM and 0.1 mM CaCl$_2$ were prepared as titration solutions. The protein and buffer solutions were lyophilized and re-hydrated repeatedly by adding D$_2$O to ensure complete H/D exchange. The fully H/D exchanged protein was applied unto a ZnSe ATR crystal and purged with D$_2$O vapor to ensure hydration of the protein. Titration experiments were carried out by adding 10 μL of 0.1 mM or 0.5 mM CaCl$_2$ solution to 190 μL of D$_2$O.

Figure 11:
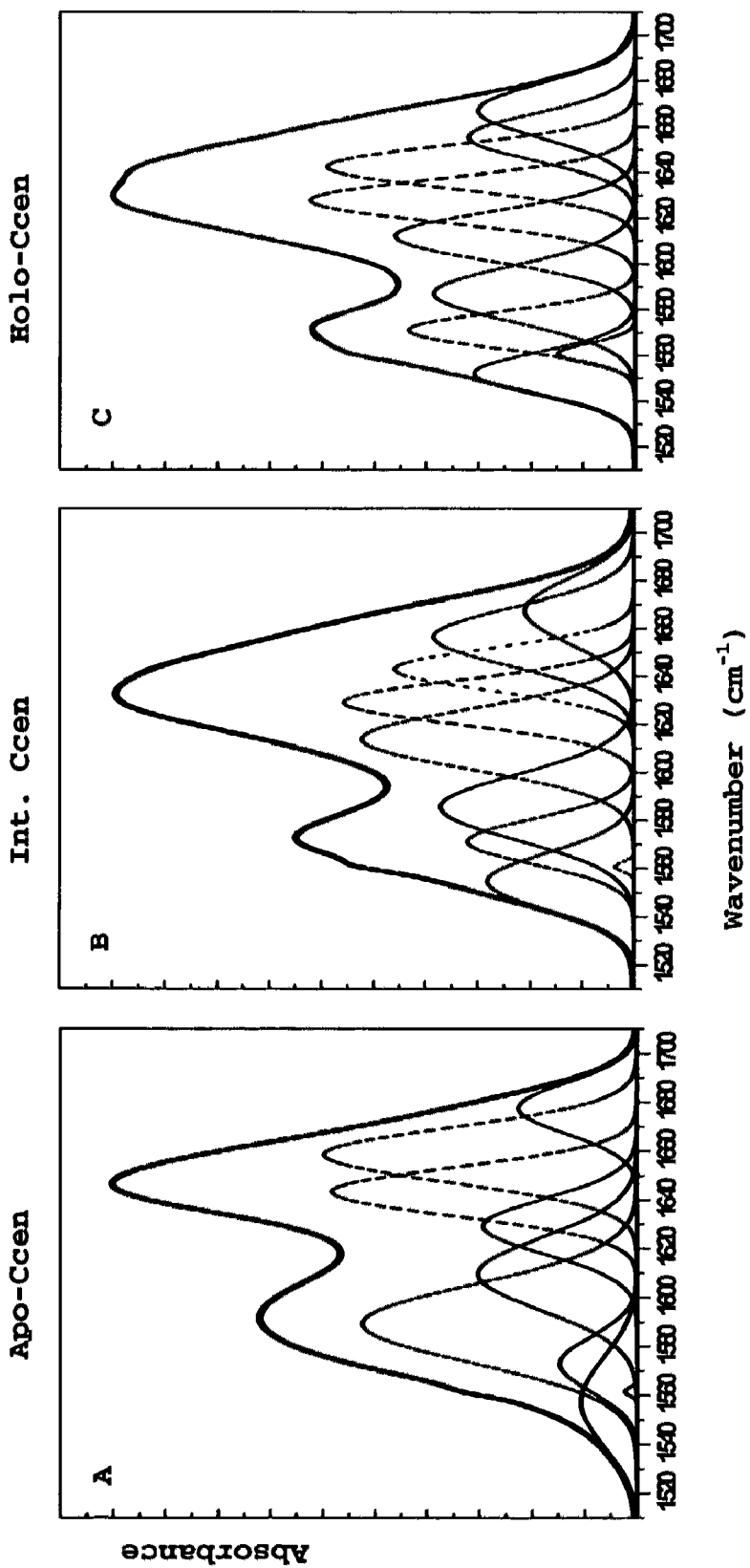
FIG. 11 shows curvefit plots for full-length Ccen at different calcium concentrations.
Figure 12:
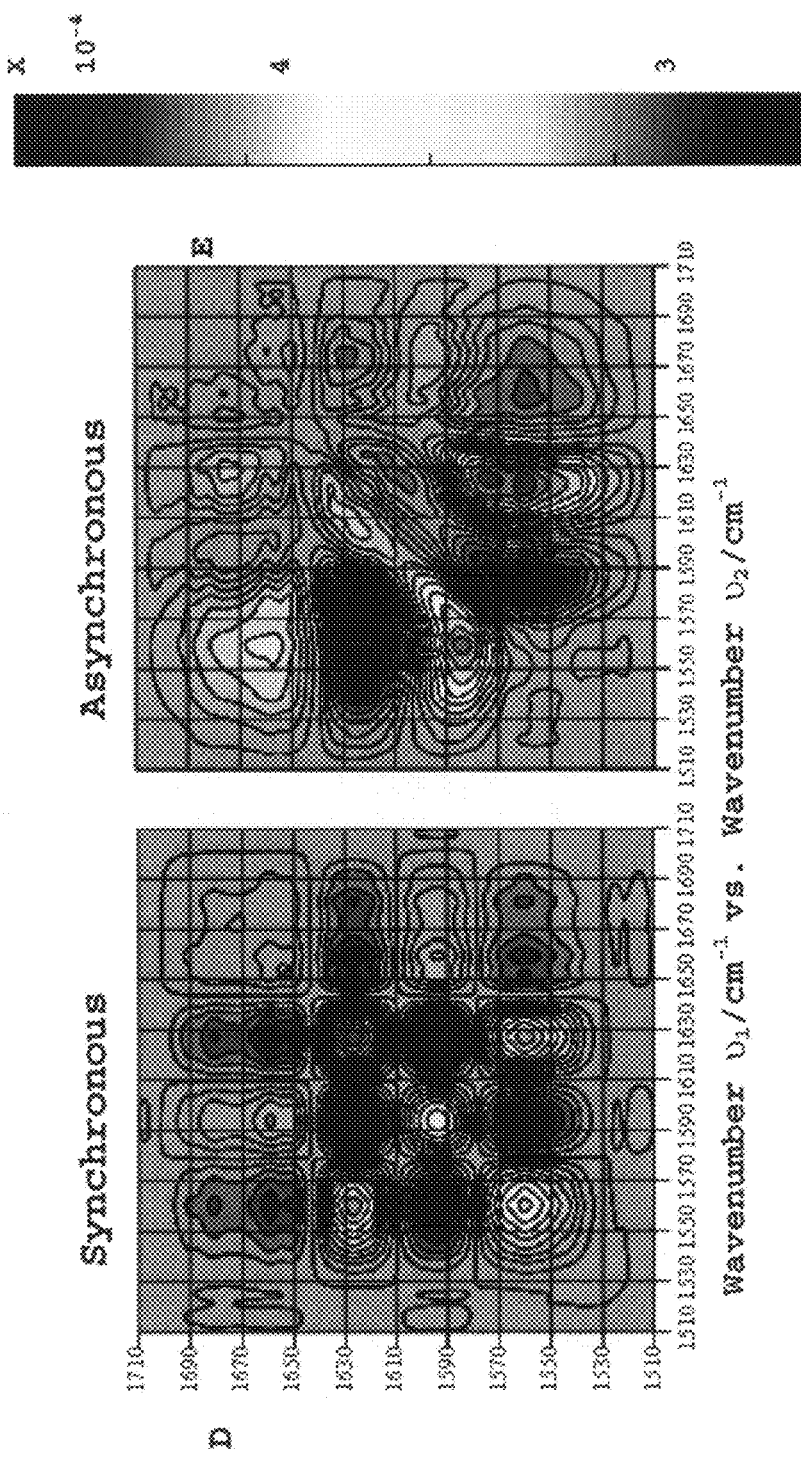
FIG. 12 shows synchronous and asynchronous 2DCOS plots for full-length Ccen.

The spectral features observed in the amide I' band indicate the mechanism of self-association of this protein by monitoring the vibrational modes associated with the backbone, as well as, the side chains. The major calcium contributions to the conformational changes in the curve-fit analysis for Ccen are shown in FIG. 11; using 2DCOS synchronous plots the correlation between the aspartate side chain modes involved in the coordination with calcium and the backbone are clearly established. The aspartate modes changed prior the 1670 cm$^{-1}$ and 1620 cm$^{-1}$ peaks associated with aggregation as seen on FIG. 12. Thus, it was confirmed that the aggregation of this protein is calcium dependent.

EXAMPLE 5

C-Centrin/Melittin Complex

Figure 13:
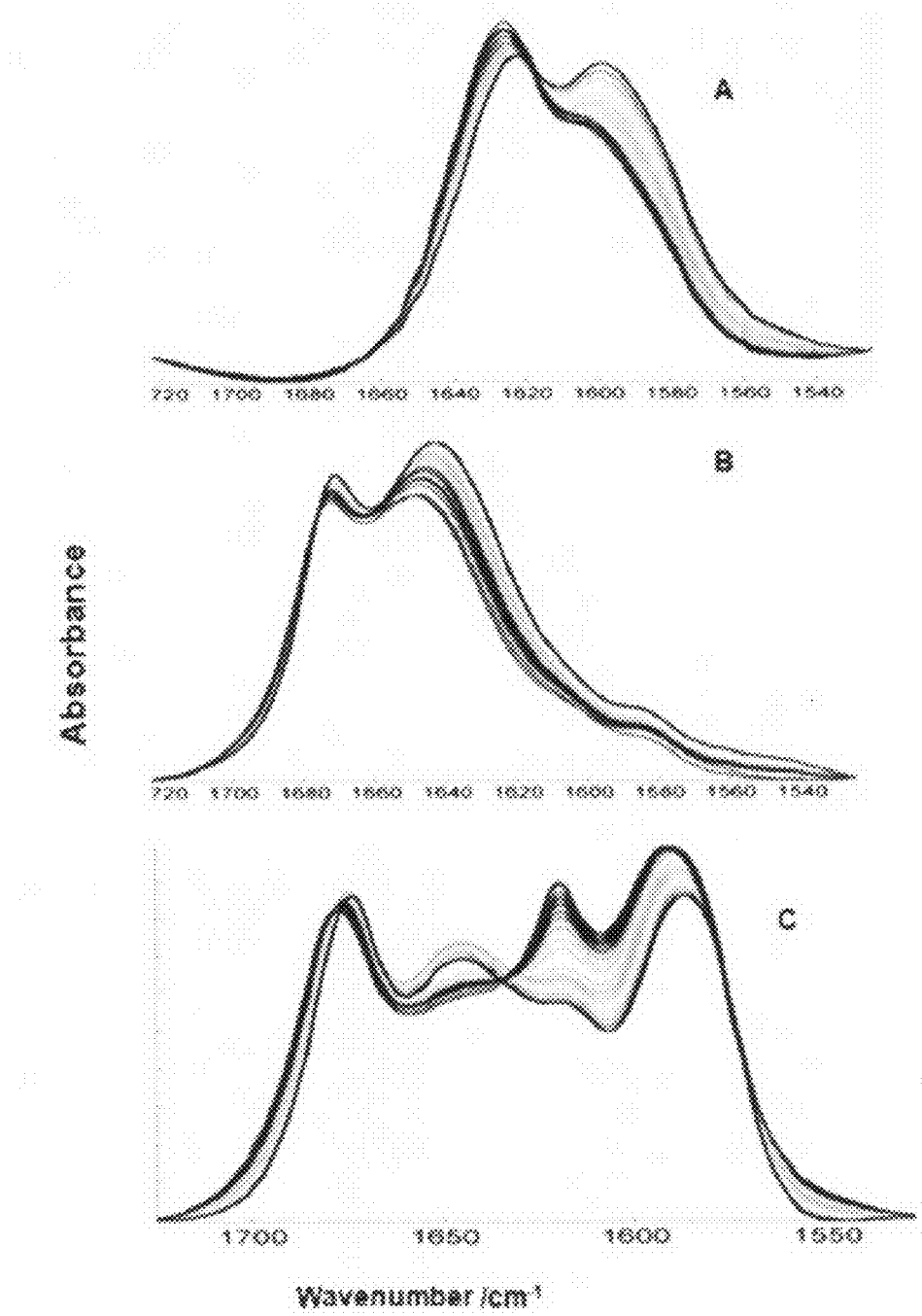
FIG. 13 shows overlaid spectra of C-centrin, Mellitin and C-Centrin-mellitin complex in the Spectral region of 1725-1525 $cm^{-1}$.

In the presence of calcium, centrin forms a complex with mellitin (MLT) which is an amphiphilic peptide from bee venom. Calcium binding proteins in general have an unusually high thermal denaturation temperature, at times a conformational transition (pre-transition) is observed prior to melting. Transition temperature upon complex formation between C=0 homogeneously labeled centrin and a 26-residue peptide, mellitin, were studied in aqueous D$_2$O solution as a function of temperature using Fourier transform-infrared (FT-IR) spectroscopy and 2DCOS. Spectral features studied in the spectral region amide I (1720-1550 cm$^{-1}$) for C-centrin, MLT and C-centrin/MLT complex are shown in FIG. 13. The observed shift of approximately 38 cm$^{-1}$ for the amide I'* band, (asterisk denotes C=0 labeled protein) comprised almost exclusively of C=0 stretching mode when the protein sample is completely H/D exchanged. A spectral overlay of the thermal dependence of C-centrin is also shown in FIG. 13. The band assignment for this C-labeled protein spectra, must take into account the isotope shift at 1625 cm$^{-1}$ (β-turns* or loops*) and at 1600 cm$^{-1}$ (α-helix*). Thus, if aggregation were present a shoulder at approximately 1570 cm$^{-1}$ (aggregation*) would be observed as well for the C-centrin spectra shown in FIG. 13. An overlay of the MLT thermal dependence study is also shown in FIG. 13. Spectral features for MLT include random coil (1680 cm$^{-1}$) and helical structural motif (1640 cm$^{-1}$) for the amide I band. The spectral overlay of the protein/peptide complex is also shown in FIG. 13. The isotope labeling of one of the components allows for the simultaneous study of the C-Centrin and MLT in the complex. The relative thermal stability for these proteins can also be established by plotting wavenumber of the amide I band as a function of temperature. No aggregation is observed for the single component thermal dependence studies, yet for the protein/peptide complex the aggregation band is observed to increase as temperature is increased. From the spectral overlay shown in FIG. 13, it is difficult to establish which component of the complex is aggregating.

Figure 14:
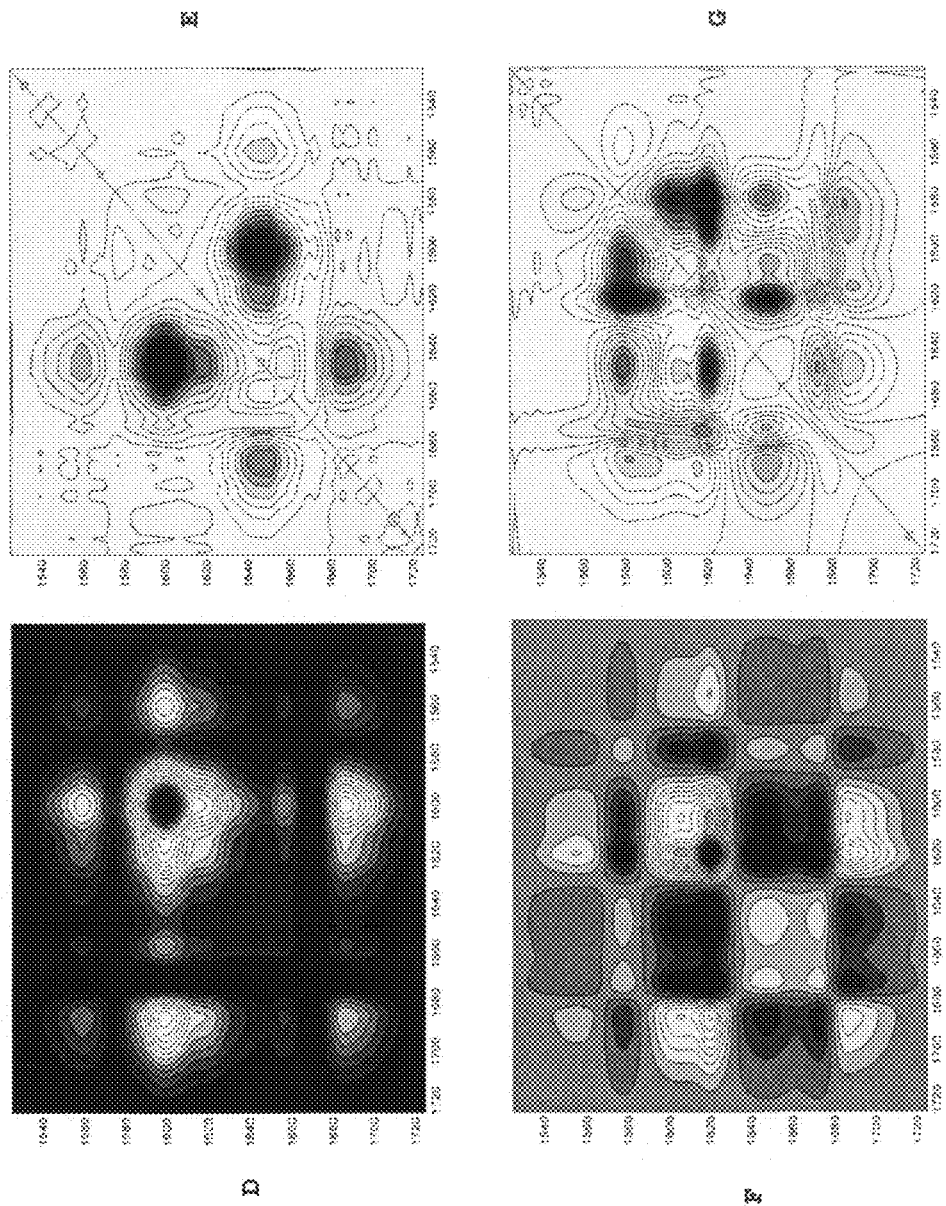
FIG. 14 shows 2DCOS synchronous and asynchronous plots of C-Centrin-mellitin complex, and 2DCOS spectra of the region 2-50° C. and Synchronous 2DCOS spectra of the region 50-96° C.

2DCOS has been used successfully in this study to establish that it is the mellitin component which is aggregating in the protein/peptide complex, as shown in FIG. 14 by separating the spectral data set into two temperature regions (2-50° C.) and (50-96° C.). The synchronous plots for C-centrin/MLT for the temperature range of 2-50° C. as seen on FIG. 14 contains the following autopeaks representative of C-centrin and MLT: 1550 cm$^{-1}$ (glutamate side chain, C-centrin), 1600 cm$^{-1}$ ($\alpha$-helix*, C-centrin), low intensity autopeak at 1620 cm$^{-1}$ (aggregation, MLT), low intensity 1650 cm$^{-1}$ ($\alpha$-helix, MLT) and 1690 cm$^{-1}$ (random coil, MLT). The order of events for this temperature range (2-50° C.) was the following: aspartates (1580 cm$^{-1}$) within the calcium binding loops of centrin begin to change after the $\alpha$-helix* secondary structural motifs of centrin, while in MLT, $\beta$-turns appear (1670 cm$^{-1}$) prior to the helix-coil transition of centrin. During the temperature range of 50-96° C. the synchronous plot is comprised of the following autopeaks: 1580 cm$^{-1}$ (aspartate, centrin), 1600 cm$^{-1}$ ($\alpha$-helix*, C-centrin), high intensity autopeak at 1620 cm$^{-1}$ (aggregation, MLT), 1650 cm$^{-1}$ ($\alpha$-helix, MLT and random coil, centrin), 1670 cm$^{-1}$ ($\beta$-turns, MLT) and 1690 cm$^{-1}$ (random coil, MLT) as shown in FIG. 14. The order of events for this temperature range can be established using the asynchronous and synchronous plots phase information confirms the order of events mentioned above and suggests that the aggregation of MLT is dependent on the interaction with
centrin the aspartates (1580 cm$^{-1}$) found primarily in the calcium binding loops change after the helix to random coil transition for MLT has occurred. The aggregation (1620 cm$^{-1}$) MLT and $\beta$-turns at (1670 cm$^{-1}$) occur prior to the aspartates (1580 cm$^{-1}$) within the centrin. This event occurs prior to the thermal denaturation of centrin.

In each case discussed within this method application, FT-IR spectroscopy and 2DCOS have been used to establish the presence of aggregation, and what secondary structural changes occurred associated with the aggregation of the protein. The mechanism by which the aggregation occurred whether it was due to thermal denaturation, salt content, or protein/protein interaction and if certain side chains were key in the process of aggregation can be determined using the proposed method. In the Bio-Pharmaceutical Industry the automated process would generate the 2DCOS plots which could be easily compared with the viable protein 2DCOS plots. The presence of aggregation or denatured protein would generate a plot or image which could be analyzed to determine where in the process of manufacturing would need a change in protocol as depicted in FIG. 2. Also in two of the examples we have summarized in Table 2 (C-Ccen-MLT complex) the spectral intensities, temperature and structurally intact (unchanged) fraction of the protein used to determine the percent of aggregation.

The combined results obtained from the 2DCOS and the fraction of intensity change for each structural domain, Arg and Tyr side chains shown in the Table of FIG. 6, due to thermal denaturation (spectra 4-20) and aggregation (highlighted, spectra 21-25) have led to the quantitative determination of almost 14% aggregation as follows:

$$f_{non-aggregated} = \frac{I_i}{I_{largest}}$$

where, $I_i$ are individual intensities during the aggregation process and $I_{largest}$ is the largest intensity within the data set which defines the limit of the aggregation process.

$$100 \times (f_f - f_o)_{aggregation} = (0.91 - 0.77)_{1615} \times 100 = 14\% \text{ aggregation}$$

where, and $f_o$ and $f_f$ are the initial and final fractions, respectively for peak with highest intensity changes (1615 cm$^{-1}$) that reports the aggregation process, which is highlighted.

The aggregation is primarily due to the $\beta$-sheets and $\beta$-turns once thermal denaturation of the domains has occurred. This result is obtained assuming the intensity is proportional to the protein concentration and that the molar extinction coefficient observed within the spectral range of 1700-1500 cm$^{-1}$ is constant.

We have been able to also define and quantify the extent of aggregation within a binary mixture of proteins demonstrating the uniqueness of the inventive method. MLT's helical domain is aggregating within the complex while, centrin is observed to have greater helical content during the aggregation process of mellitin. We defined the reporter peak as MLT's approximately 1619 cm$^{-1}$ (aggregation) as shown in the Table of FIG. 15. As control we used MLT's approximately 1677 cm$^{-1}$ (random coil). Also listed is MLT's 1645.5 cm$^{-1}$ (helical) peak as the principal domain involved in the aggregation process.

The changes due to thermal denaturation and aggregation (highlighted, spectra 8-24) have led to the quantitative determination of almost 27% aggregation as follows:

$$f_{non-aggregated} = \frac{I_i}{I_{largest}}$$

where, $I_i$ are individual intensities during the aggregation process and $I_{largest}$ is the largest intensity within the data set which defines the limit of the aggregation process.

$$100 \times (f_f - f_o)_{aggregation\ process} = (1.0 - 0.73)_{1619} \times 100 = 27\% \text{ aggregation}$$

where $f_o$ and $f_f$ are the initial and final fractions, respectively, respectively for each peak (1685 cm$^{-1}$ and 1615 cm$^{-1}$) that reports the aggregation process, which is highlighted.

FT-IR spectroscopy and 2DCOS are instrumental in establishing the mechanism of aggregation, protein/protein interaction, and establishing the molecular level changes that occur in a protein during a perturbation process. These questions are essential in understanding the biological function of a protein.

While the preferred embodiments of the present invention have been illustrated and described, it will be clear that the present invention is not limited to these embodiments only. Numerous modifications, changes, variations, substitutions and equivalents will be apparent to those skilled in the art without departing from the spirit and scope of the present invention as described in the claims.

We claim:

1. A method for determining aggregation, stability and viability of proteins, peptides or peptoids comprising:
   obtaining temperature variable FT-IR spectra of said proteins, peptides or peptoids,
   applying 2-dimensional correlation analysis (2DCOS), generating synchronous and asynchronous plots for said proteins, peptides or peptoids,
   identifying in said synchronous plot positive cross peaks that correlate with auto peaks associated with aggregation of said proteins, peptides or peptoids; and
   using the identified peak intensities of the corresponding FT-IR spectra to determine the amount of aggregation of said proteins, peptides or peptoids.

2. The method of claim 1, wherein the mechanism of aggregation of said proteins, peptides or peptoids is derived by analyzing said asynchronous plot.

3. The method of claim 1, wherein said FT-IR spectra is obtained by a process comprising one of: Transmission FT-IR and Attenuated Total Reflectance FT-IR.

4. The method of claim 2, wherein said asynchronous plot is analyzed to determine the order of events during the aggregation of said proteins, peptides or peptoids and the mechanism of aggregation of said proteins, peptides or peptoids in at least one of: an aqueous solvent and lipidic environment.

5. The method of claim 1, wherein said identified peak intensities are used to determine a temperature range in which a change in intensity is observed.

6. The method of claim 5, further comprising defining the intensity limits of said aggregation process, and determining a fractional value for each intensity value within said intensity limits defined by the ratio between each intensity value and the largest intensity value within said limits.

7. The method of claim 6, further comprising identifying the initial and final fractional values as defined by said limits for each peak present in the aggregation process; and determining the amount of aggregation based at least on said initial and final fractional values.

8. The method of claim 1, wherein reporter spectral peaks are defined at 1610-1625 cm−1 and 1670-1685 cm−1 located in the amide I band.

9. The method of claim 1, further comprising a mixture of said proteins, peptides or peptoids.

10. The method of claim 9, wherein said mixture comprises a 13C isotope labeled protein having a reporter peak defined at 1670-1525 cm−1 within the Amide I* band.

11. The method of claim 1, wherein the amount of aggregation in said proteins, peptides or peptoids is determined based on the peaks of the secondary structure changes of said proteins, peptides or peptoids.

* * * * *